United States Patent
Chadeayne

(10) Patent No.: US 11,926,590 B2
(45) Date of Patent: Mar. 12, 2024

(54) CRYSTALLINE 4-HYDROXY-N,N-DI-N-PROPYLTRYPTAMMONIUM (4-HO-DPT) SALTS

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 17/998,870

(22) PCT Filed: May 19, 2021

(86) PCT No.: PCT/US2021/033143
§ 371 (c)(1),
(2) Date: Nov. 15, 2022

(87) PCT Pub. No.: WO2021/236759
PCT Pub. Date: Nov. 25, 2021

(65) Prior Publication Data
US 2023/0126343 A1    Apr. 27, 2023

Related U.S. Application Data

(60) Provisional application No. 63/080,325, filed on Sep. 18, 2020, provisional application No. 63/027,675, filed on May 20, 2020.

(51) Int. Cl.
*C07D 209/16*    (2006.01)

(52) U.S. Cl.
CPC ........ *C07D 209/16* (2013.01); *C07B 2200/13* (2013.01)

(58) Field of Classification Search
CPC .................................................. C07D 209/16
See application file for complete search history.

(56) References Cited

U.S. PATENT DOCUMENTS

| | | |
|---|---|---|
| 2018/0021326 A1 | 1/2018 | Stamets |
| 2018/0221396 A1 | 8/2018 | Chadeayne |
| 2019/0142851 A1 | 5/2019 | Chadeayne |

OTHER PUBLICATIONS

International Preliminary Report on Patentability in International Application No. PCT/US2021/033143, dated Dec. 1, 2022.
International Search Report and Written Opinion in International Application No. PCT/US2021/033143 dated Nov. 18, 2021.
Carhart-Harris, R. L. & Goodwin, G. M. (2017). Neuropsychopharmacology, 42, 2105-2113.
Chadeayne, A. R., Golen, J. A. & Manke, D. R. (2019a). Acta Cryst. E75, 900-902.
Chadeayne, A. R., Golen, J. A. & Manke, D.R. (2019b). IUCrData, 4, x190962.
Chadeayne, A. R., Golen, J. A. & Manke, D. R. (2019c). Psychedel. Sci. Rev. https:/ /psychede!iw::view. com/the-crystal-structure-of-4-aco-dmt-fumarate/.
Chadeayne, A. R., Pham, D. N. K., Golen, J. A. & Manke, D.R. (2019). Acta Cryst. E75, 1316-1320.
Dolomanov, 0. V., Bourhis, L. J., Gildea, R. J., Howard, J. A. K. & Puschmann, H. (2009). J. Appl. Cryst. 42, 339-341.
Falkenberg, G. (1972). Acta Cryst. B28, 3075-3083.
Petcher, T. J. & Weber, H. P. (1974). J. Chem. Soc. Perkin Trans. 2, pp. 946-948.
Repke, D. B., Ferguson, W. J. & Bates, D. K. (1977). J. Heterocycl. Chem. 14, 71-74.
Sheldrick, G. M. {2015a). Acta Cryst. A71, 3-8.
Sheldrick, G. M. (2015b). Acta Cryst. C71, 3-8.
Shulgin, A. T., & Shulgin, A. (1997). Tihkal. La Fayette: Transform Press.
Weber, H. P. & Petcher, T. J. (1974). J. Chem. Soc. Perkin Trans. 2, pp. 942-946.
Westrip, S. P. (2010). J. Appl. Cryst. 43, 920-925.
Sammeta et al., (2020) "The hydrochloride salt of 4-hydroxy-N,N-di-npropyltryptamine (4-HO-DPT)".
Chadeayne, A. R., Pham, D. N. K., Golen, J. A. & Manke, D.R. (2019d). "Bis(4-hydroxy-N,N-di-n-propyltryptammonium) fumarate tetrahydrate".

*Primary Examiner* — Rebecca L Anderson
(74) *Attorney, Agent, or Firm* — Raphael Bellum PLLC

(57) ABSTRACT

This disclosure relates to crystalline bis(4-hydroxy-N,N-d-n-propyltryptammonium)fumarate tetrahydrate (4-HO-DPT fumarate-4H$_2$O) and to Crystalline 4-hydroxy-N,N-di-n-propyl-tryptammonium chloride (4-HO-DPT chloride). Compositions containing crystalline 4-HO-DPT fumarate-4H$_2$O or crystalline 4-HO-DPT chloride, and methods of use are disclosed.

5 Claims, 7 Drawing Sheets

CRYSTALLINE 4-HYDROXY-N,N-DI-N-PROPYLTRYPTAMMONIUM (4-HO-DPT) SALTS

CROSS-REFERENCE TO RELATED APPLICATIONS

This application claims priority to U.S. Provisional Application No. 63/027,675 filed on May 20, 2020 and to U.S. Provisional Application No. 63/080,325 filed on Sep. 18, 2020, the disclosures of which are incorporated by reference.

TECHNICAL FIELD

This disclosure relates to crystalline bis(4-hydroxy-N,N-di-n-propyltryptammonium) fumarate tetrahydrate (4-HO-DPT fumarate.4H$_2$O), and to crystalline 4-hydroxy-N,N-di-n-propyl-tryptammonium chloride (4-HO-DPT chloride); to pharmaceutical compositions containing them and to methods of treatment/therapeutic uses of crystalline 4-HO-DPT fumarate.4H$_2$O and of crystalline 4-HO-DPT chloride.

BACKGROUND OF THE INVENTION

4-Hydroxy-N,N-di-n-propyltryptamine, or 4-HO-DPT, is a derivative of psilocin, which is the primary active psychedelic in "magic" mushrooms. Psilocin is the metabolite of psilocybin and its synthetic analogue psilacetin and is a serotonin-2a agonist which results in its mood-altering effects. Tryptamines, both naturally occurring [Psilocybin (Weber & Petcher, 1974), Psilocin (Petcher & Weber, 1974), and DMT (Falkenberg, 1972)] and their synthetic derivatives [Psilacetin (Chadeayne et al. 2019a,b), MPT (Chadeayne et al. 2019c), MiPT, and 4-HO-MiPT (Chadeayne, Pham et al. 2019)] have garnered a great deal of interest because of their potential to treat depression and post-traumatic stress disorder (PTSD) (Carhart-Harris & Goodwin, 2017). Although several structural analogs of psilocin have been previously reported (by, e.g., Shulgin) these compounds were not rigorously purified or characterized, leaving substantial doubt regarding their purity and identity. As a result, unknown or unappreciated features of the solid-state structures (e.g., solvate form) have resulted in ambiguity and errors in downstream research. For example, failing to precisely identify the solvate or salt form of a molecule affects the molecular mass calculations and, therefore binding affinity, potency, and dosing calculations. In a February 2020 study published in the *Journal of Natural Products*, Dr. Alexander Sherwood of the Usona Institute noted that psychedelic research had been impeded by a lack of access to pure, well-characterized research chemicals. It is not possible conduct accurate biologic studies or clinical trials without using pure, well-characterized compounds.

Crystalline forms of compounds are ideal for downstream research and pharmaceutical development because they often provide advantages in terms of handling, stability, purification, physical characterization, and formulation. Many crystalline compounds are suitable for x-ray diffraction experiments, through which the solid-state structure of the molecule can be empirically determined from physical data. The solid-state structures of bioactive tryptamine molecules are significant because they define each molecule's physical identity, thereby providing the gold standard for physical characterization, laying a foundation for all downstream research. In addition to accurately defining the atomic composition and arrangement of the molecule, structural characterization enables a variety of in silico modeling experiments, which are important in assessing each molecule's biological and clinical properties, e.g., via structure-activity relationships.

The compound 4-OH-DPT is a structural analog of psilocin. Shulgin synthesized 4-HO-DPT as the free base in about 50% yield and expressed remorse that further studies were confounded because "[i]t's a shame that the compound is rather difficult to make." (Shulgin, pp. 479-80). To address the unmet need for pure, well-characterized forms of 4-HO-DPT, we report the preparation and characterization of crystalline forms of 4-HO-DPT herein.

SUMMARY OF THE INVENTION

This disclosure relates to crystalline bis(4-hydroxy-N,N-di-n-propyltryptammonium) fumarate tetrahydrate (4-HO-DPT fumarate.4H$_2$O). Crystalline 4-HO-DPT fumarate.4H$_2$O may be characterized by at least one of: a monoclinic, P2$_1$/n space group at a temperature of about 200 K; unit cell dimensions a=8.3495(8) Å, b=12.5138(11) Å, c=18.6631(17) Å, α=90°, β=100.902(3)°, and γ=90°; an x-ray powder diffraction (XRPD) pattern substantially similar to FIG. 4; and an X-ray powder diffraction pattern characterized by peaks at 8.5, 9.6, and 10.9°2θ±0.2°2θ.

This disclosure also relates to crystalline 4-hydroxy-N,N-di-n-propyl-tryptammonium chloride (4-HO-DPT chloride). Crystalline 4-HO-DPT chloride characterized by at least one of: a triclinic, P⁻1 at a temperature of about 273 K; unit cell dimensions a=7.860 (3) Å, b=10.439 (4) Å, c=11.713 (5) Å, α=76.236 (14) °, β=73.653 (13)°, and γ=68.852 (12)°.

The disclosure further relates to a composition comprising crystalline 4-HO-DPT fumarate.4H$_2$O or crystalline 4-HO-DPT chloride according to this disclosure and an excipient.

The disclosure also provides a composition comprising crystalline 4-HO-DPT fumarate.4H$_2$O or crystalline 4-HO-DPT chloride according to this disclosure as a first component and a second component selected from at least one of (a) a purified psilocybin derivative, (b) a purified cannabinoids, or (c) a purified terpene.

The disclosure also relates to a method of preventing or treating a psychological disorder comprising the step of administering to a subject in need thereof a therapeutically effective amount of crystalline 4-HO-DPT fumarate.4H$_2$O or crystalline 4-HO-DPT chloride according to this disclosure or a composition according to this disclosure.

The disclosure further relates to a method of preventing or treating inflammation and/or pain comprising the step of administering to a subject in need thereof a therapeutically effective amount of crystalline 4-HO-DPT fumarate.4H$_2$O or crystalline 4-HO-DPT chloride according to this disclosure or a composition according to this disclosure.

As used herein, the term "a subject in need thereof" refers a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

Compounds

Figure 1:
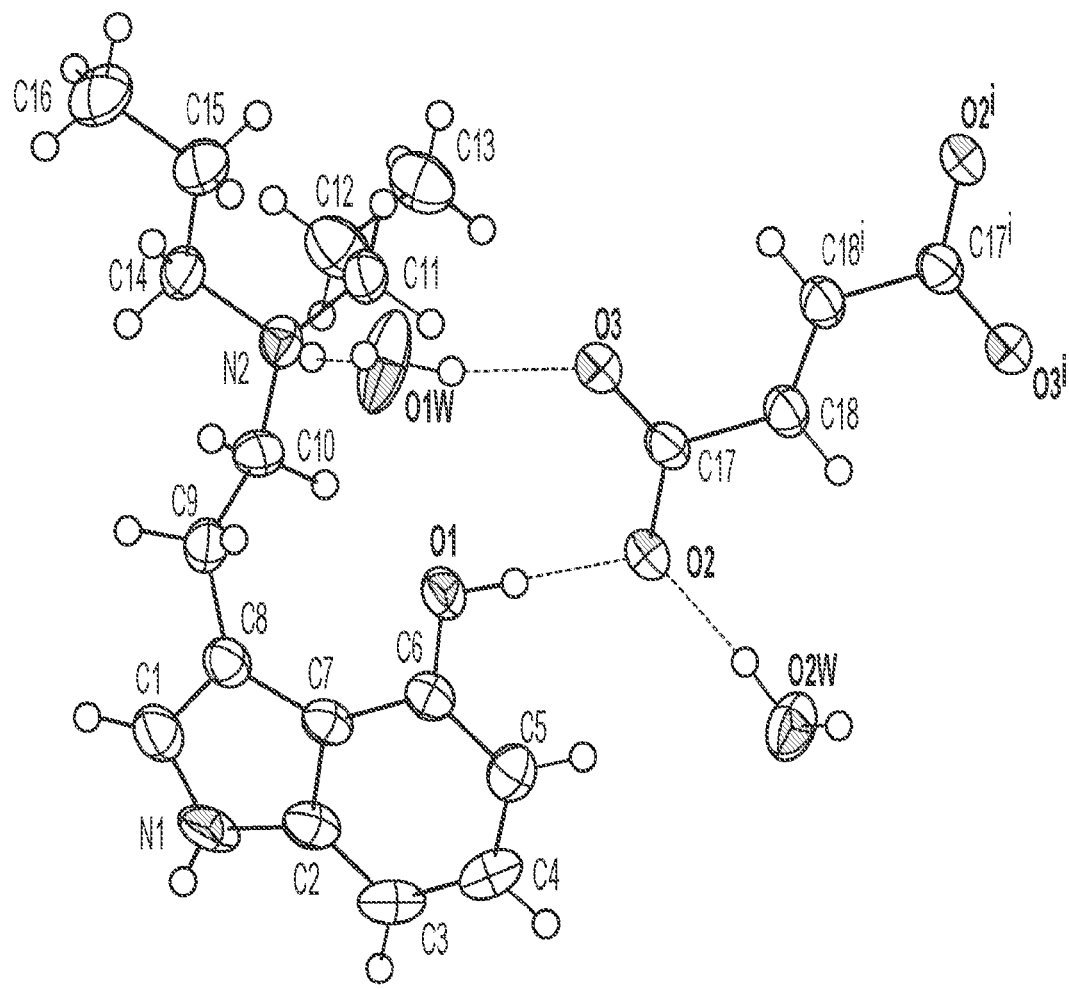
FIG. 1 shows the molecular structure of 4-HO-DPT fumarate.4H$_2$O, showing the atomic labeling.

This disclosure relates to crystalline bis(4-hydroxy-N,N-di-n-propyltryptammonium) fumarate tetrahydrate (4-HO-DPT fumarate.4H$_2$O) and to crystalline 4-hydroxy-N,N-di-n-propyl-tryptammonium chloride (4-HO-DPT chloride), and to pharmaceutical compositions containing crystalline 4-HO-DPT fumarate.4H$_2$O or containing crystalline 4-HO-DPT chloride according to the disclosure. The therapeutic uses of crystalline 4-HO-DPT fumarate.4H$_2$O and of crystalline 4-HO-DPT chloride according to the disclosure are described below as well as compositions containing each of them. Crystalline 4-HO-DPT fumarate.4H$_2$O and the methods used to characterize it are described in the examples below. Crystalline 4-HO-DPT chloride and the methods used to characterize it are described in the examples below.

This disclosure also relates to bis(4-hydroxy-N,N-di-n-propyltryptammonium) fumarate tetrahydrate (4-HO-DPT fumarate.4H$_2$O) and to 4-hydroxy-N,N-di-n-propyl-tryptammonium chloride (4-HO-DPT chloride), and to pharmaceutical compositions containing 4-HO-DPT fumarate.4H$_2$O or containing 4-HO-DPT chloride according to the disclosure. In some embodiments, 4-HO-DPT fumarate and 4-HO-DPT chloride are crystalline.

4-HO-DPT fumarate.4H$_2$O has the following chemical formula:

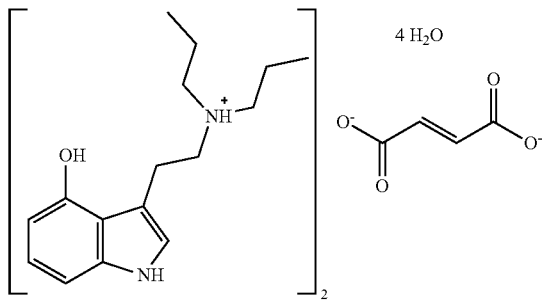

4-HO-DPT chloride has the following chemical formula:

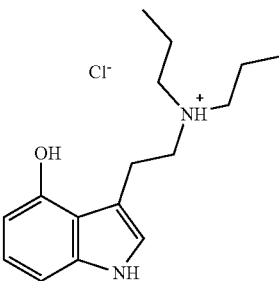

The disclosure further relates to fumarate salts of 4-HO-DPT. Exemplary fumarate salts of 4-HO-DPT include the fumarate and hemifumarate salts, and hydrates and solvates thereof. In certain embodiments, the fumarate salt of 4-HO-DPT is crystalline. In some embodiments, the fumarate salt of 4-HO-DPT is bis(4-hydroxy-N,N-di-n-propyltryptammonium) fumarate tetrahydrate (4-HO-DPT fumarate.4H$_2$O). In some embodiments, the fumarate salt of 4-HO-DPT is crystalline 4-HO-DPT fumarate.4H$_2$O.

The disclosure further discloses salts of 4-HO-DPT. Exemplary salts of 4-HO-DPT include fumarate and chloride salts, and solvates (e.g., hydrates) thereof. In certain embodiments, the salt of 4-HO-DPT is crystalline. In some embodiments, the salt of 4-HO-DPT is 4-hydroxy-N,N-di-n-propyl-tryptammonium chloride (4-HO-DPT chloride). In some embodiments, the salt of 4-HO-DPT is crystalline 4-HO-DPT chloride.

Methods of Treatment and Therapeutic Uses

4-HO-DPT fumarate.4H$_2$O and 4-HO-DPT chloride according to the disclosure, crystalline forms thereof, and the methods and the compositions (e.g., pharmaceutical compositions) are used to regulate the activity of a neurotransmitter receptor by administering a therapeutically effective dose of 4-HO-DPT fumarate.4H$_2$O or of 4-HO-DPT chloride of the disclosure. In one embodiment, crystalline 4-HO-DPT fumarate.4H$_2$O and crystalline 4-HO-DPT chloride according to the disclosure, and the methods and the compositions (e.g., pharmaceutical compositions) are used to treat inflammation and/or pain by administering a therapeutically effective dose of crystalline 4-HO-DPT fumarate.4H$_2$O or of crystalline 4-HO-DPT chloride of the disclosure.

Methods of the disclosure also related to the administration of a therapeutically effective amount of crystalline 4-HO-DPT fumarate.4H$_2$O or crystalline 4-HO-DPT chloride to prevent or treat a disease or condition, such as those discussed below for a subject in need of treatment. Crystalline 4-HO-DPT fumarate.4H$_2$O or crystalline 4-HO-DPT chloride may be administered neat or as a composition comprising crystalline 4-HO-DPT fumarate.4H$_2$O or crystalline 4-HO-DPT chloride as discussed below.

Crystalline 4-HO-DPT fumarate.4H$_2$O or crystalline 4-HO-DPT chloride may be used to prevent and/or treat a psychological disorder. The disclosure provides a method for preventing and/or treating a psychological disorder by administering to a subject in need thereof a therapeutically effective amount of crystalline 4-HO-DPT fumarate.4H$_2$O or of crystalline 4-HO-DPT chloride, including the exemplary embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Crystalline 4-HO-DPT fumarate.$4H_2O$ or crystalline 4-HO-DPT chloride may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of crystalline 4-HO-DPT fumarate.$4H_2O$ or of crystalline 4-HO-DPT chloride, including the exemplary embodiments discussed above.

Crystalline 4-HO-DPT fumarate.$4H_2O$ or of crystalline 4-HO-DPT chloride may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline 4-HO-DPT fumarate.$4H_2O$ or of crystalline 4-HO-DPT chloride, including the exemplary embodiments discussed above.

Crystalline 4-HO-DPT fumarate.$4H_2O$ or crystalline 4-HO-DPT chloride may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline 4-HO-DPT fumarate.$4H_2O$ or of crystalline 4-HO-DPT chloride, including the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Crystalline 4-HO-DPT fumarate.$4H_2O$ or crystalline 4-HO-DPT chloride may be used to modulate activity of a mitogen activating protein (MAP), comprising administering a composition of the invention. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-y, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

Crystalline 4-HO-DPT fumarate.$4H_2O$ or crystalline 4-HO-DPT chloride may be used to modulate neurogenesis, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Crystalline 4-HO-DPT fumarate.$4H_2O$ or crystalline 4-HO-DPT chloride may be used to modulate neurite outgrowth, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

Compositions

The disclosure also relates to compositions comprising an effective amount of 4-HO-DPT fumarate.$4H_2O$ or 4-HO-DPT chloride, including its exemplary embodiments discussed above, and an excipient (e.g., a pharmaceutically-acceptable excipient). In another embodiment, the disclosure also relates to pharmaceutical compositions comprising a therapeutically effective amount of 4-HO-DPT fumarate.$4H_2O$ or 4-HO-DPT chloride, including its exemplary embodiments discussed above, and a pharmaceutically acceptable excipient (also known as a pharmaceutically acceptable carrier). As discussed above, a 4-HO-DPT compound of the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains 4-HO-DPT fumarate.4H$_2$O or 4-HO-DPT chloride. The composition may be, for example, a tablet, capsule, liquid suspension, injectable, topical, or transdermal. The compositions generally contain, for example, about 1% to about 99% by weight of 4-HO-DPT fumarate.4H$_2$O or 4-HO-DPT chloride and, for example, 99% to 1% by weight of at least one suitable pharmaceutically acceptable excipient. In one embodiment, the composition may be between about 5% and about 75% by weight of 4-HO-DPT fumarate.4H$_2$O or 4-HO-DPT chloride, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, a 4-HO-DPT compound of the disclosure may be used as the "first purified psilocybin derivative" in the compositions described in US 2018/0221396 A1 and US 2019/0142851 A1. Accordingly, this disclosure provides a composition comprising: a first component comprising at least one 4-HO-DPT compound of the disclosure; at least one second component selected from at least one of (a) a serotonergic drug, (b) a purified psilocybin derivative, (c) a purified cannabinoid or (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising at least one 4-HO-DPT compound of the disclosure with a second component selected from at least one of (a) a serotonergic drug, (b) a purified psilocybin derivative, (c) a purified cannabinoid, or (d) a purified terpene, the compositions represent particular embodiments of the invention. Compositions having as a first component at least one 4-HO-DPT compound of the disclosure with a second component selected from at least one of (e) an adrenergic drug, (f) a dopaminergic drug, (g) a monoamine oxidase inhibitor, (h) a purified erinacine, (i) a purified hericenone represent additional particular embodiments of the invention represented by the compositions having the 4-HO-DPT fumarate.4H$_2$O or of 4-HO-DPT chloride compounds according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Exemplary psilocybin derivatives include but are not limited to psilocybin itself and the psilocybin derivatives described in paragraphs [0081]-[0109] of US 2018/0221396 A1 and [082]-[0110] US 2019/0142851 A1 as well as the disclosed exemplary embodiments. Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) at least one 4-HO-DPT compound of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, the 4-HO-DPT compound(s) and the second active compound(s) are each present in a therapeutically effective amount using a purposefully engineered and unnaturally occurring molar ratios. Exemplary molar ratios of the 4-HO-DPT compound of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing a 4-HO-DPT compound of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing a 4-HO-DPT compound of the disclosure may be used in place of a "purified psilocybin derivative" in the compositions described in US 2018/0221396 A1 and US 2019/0142851 A1. Accordingly, the disclosure provides a pharmaceutical formulation comprising as (a) at least one 4-HO-DPT compound of the disclosure and at least one second component selected from (a) a purified psilocybin derivative, (b) a purified cannabinoid or (c) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include SSRIs and SNRIs. Some examples of specific serotonergic drugs include the following molecules, including any salts, solvates, or polymorphs thereof: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-isopropyl-4-methoxy-N-methyl-T, N-isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivatives described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (A8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In on embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of a 4-HO-DPT compound of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 1. A4-HO-DPT compound of the disclosure may be anyone of the exemplary embodiments described above including the crystalline form one of those compounds as disclosed herein.

TABLE 1

| Second Compound | Molar ratio of a 4-HO-DPT compound:second compound | Molar ratio of a 4-HO-DPT compound:second compound | Molar ratio of a 4-HO-DPT compound:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of a 4-HO-DPT compound of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of a 4-HO-DPT compound to the second compound are shown in Table 2. A 4-HO-DPT compound of the disclosure may be any one of the exemplary embodiments described above including the crystalline form one of those compounds as disclosed herein.

TABLE 2

| Second Compound | Molar ratio of a 4-HO-DPT compound:second compound | Molar ratio of a 4-HO-DPT compound:second compound | Molar ratio of a 4-HO-DPT compound:second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of a 4-HO-DPT compound of the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L Limbird, eds., McGraw-Hill Press, 155-173 (2001), which is incorporated herein by reference. A 4-HO-DPT compound of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of a 4-HO-DPT compound of the disclosure, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, a 4-HO-DPT compound of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a 4-HO-DPT compound of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation and characterization of crystalline bis(4-hydroxy-N,N-di-n-propyltryptammonium) fumarate tetrahydrate (4-HO-DPT fumarate.4H$_2$O) and bis(4-hydroxy-N,N-di-n-propyltryptammonium) chloride (4-HO-DPT chloride) are described below.

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTLIsuite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1: Preparation and Characterization of Bis(4-Hydroxy-N,N-Di-n-Propyltryptammonium) Fumarate Tetrahydrate (4-HO-DPT Fumarate.4H$_2$O)

Preparation. Single crystals of 4-HO-DPT fumarate.4H$_2$O suitable for X-ray analysis were obtained by the slow evaporation of an aqueous solution of a commercial sample of 4-hydroxy-N,N-di-n-propyltryptamine fumarate (The Indole Shop, Canada).

Single Crystal Characterization. The single crystal data and structure refinement parameters for the crystalline structure of 4-HO-DPT fumarate.4H$_2$O measured at 200 K are reported in Table 3, below.

TABLE 3

| Crystal data | |
|---|---|
| Chemical formula | C$_{16}$H$_{25}$N$_2$O$^+$·0.5C$_4$H$_2$O$_4^{2-}$·2H$_2$O |
| M$_r$ | 354.44 |
| Crystal system, space group | Monoclinic, P2$_1$/n |
| Temperature (K) | 200 |
| a, b, c (Å) | 8.3495 (8), 12.5138 (11), 18.6631 (17) |
| β (°) | 100.902 (3) |
| V (Å$^3$) | 1914.8 (3) |
| Z | 4 |
| Radiation type | Mo Kα |
| μ (mm$^{-1}$) | 0.09 |
| Crystal size (mm) | 0.20 × 0.15 × 0.10 |
| Data collection | |
| Diffractometer | Bruker D8 Venture CMOS |
| Absorption correction | Multi-scan (SADABS; Bruker, 2016) |
| T$_{min}$, T$_{max}$ | 0.705, 0.745 |
| No. of measured, independent and observed [I > 2σ(I)] reflections | 52418, 3512, 2630 |
| R$_{int}$ | 0.061 |
| (sin θ/λ)$_{max}$ (Å$^{-1}$) | 0.604 |
| Refinement | |
| R[F$^2$ > 2σ(F$^2$)], wR(F$^2$), S | 0.046, 0.128, 1.05 |
| No. of reflections | 3512 |
| No. of parameters | 257 |
| H-atom treatment | H atoms treated by a mixture of independent and constrained refinement |
| Δρ$_{max}$, Δρ$_{min}$ (e Å$^{-3}$) | 0.59, −0.22 |

Computer programs: SAINT (Bruker, 2016), SHELXT2014 (Sheldrick, 2015a), SHELXL (Sheldrick, 2015b), OLEX2 (Dolomanov et al., 2009) and publCIF (Westrip, 2010).

FIG. 1 shows the molecular structure of 4-HO-DPT fumarate.4H$_2$O, showing the atomic labeling. Displacement ellipsoids are drawn at 50% probability level. Hydrogen bonds are shown as dashed lines. Symmetry code: (i) 2−x, 1−y, −z. The asymmetric unit contains one 4-HO-DPT cation, protonated at the dipropylamine N atom. There are also two independent water molecules, and half of a fumarate ion present.

Figure 2:
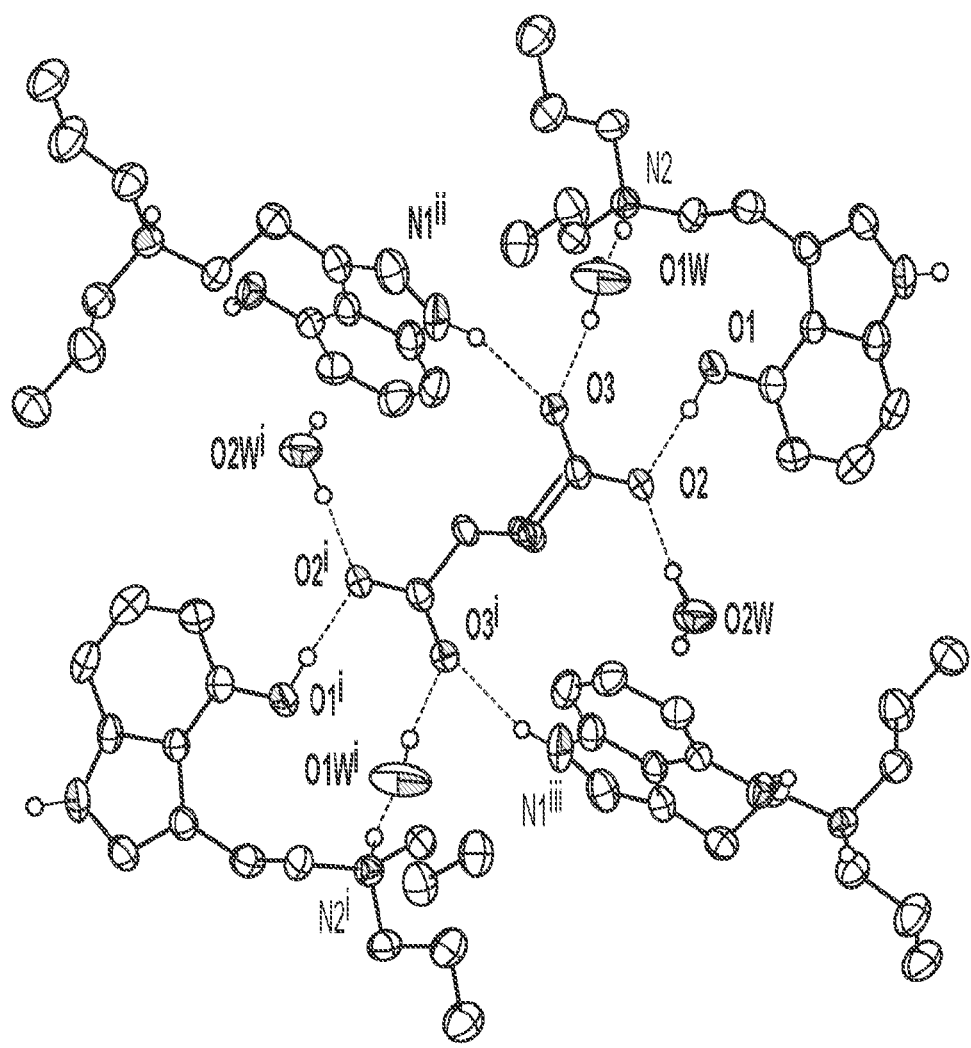
FIG. 2 shows the hydrogen bonding of the fumarate ion in the structure of 4-HO-DPT fumarate.4H$_2$O with hydrogen bonds shown as dashed lines.

FIG. 2 shows the hydrogen bonding of the fumarate ion in the structure of 4-HO-DPT fumarate.4H$_2$O, with hydrogen bonds shown as dashed lines. Displacement ellipsoids are drawn at the 50% probability level. Hydrogen atoms not involved in hydrogen bonds are omitted for clarity. Symmetry codes: (i) 2−x, 1−y, −z; (ii) −1/2+x, 1/2−y, −1/2+z; (iii) 5/2−x, 1/2+y, 1/2−z. The 4-hydroxy-N,N-di-n-propyl-tryptammonium cations, fumarate dianions and water molecules are linked to each other in an infinite three-dimensional network through hydrogen bonds (FIG. 2). Both inequivalent O atoms on the fumarate dianion (i.e., O2 and O3) accept two hydrogen bonds. One oxygen accepts hydrogen bonds from the hydroxide of the DPT cation and one water molecule. The other oxygen inter-acts with the indole N atom and the second independent water molecule. The ammonium proton hydrogen bonds with one of the water molecules. A weak O—H . . . π interaction is observed between one hydrogen atom of one of the water molecules and the six-membered ring of an adjacent indole unit.

Figure 3:
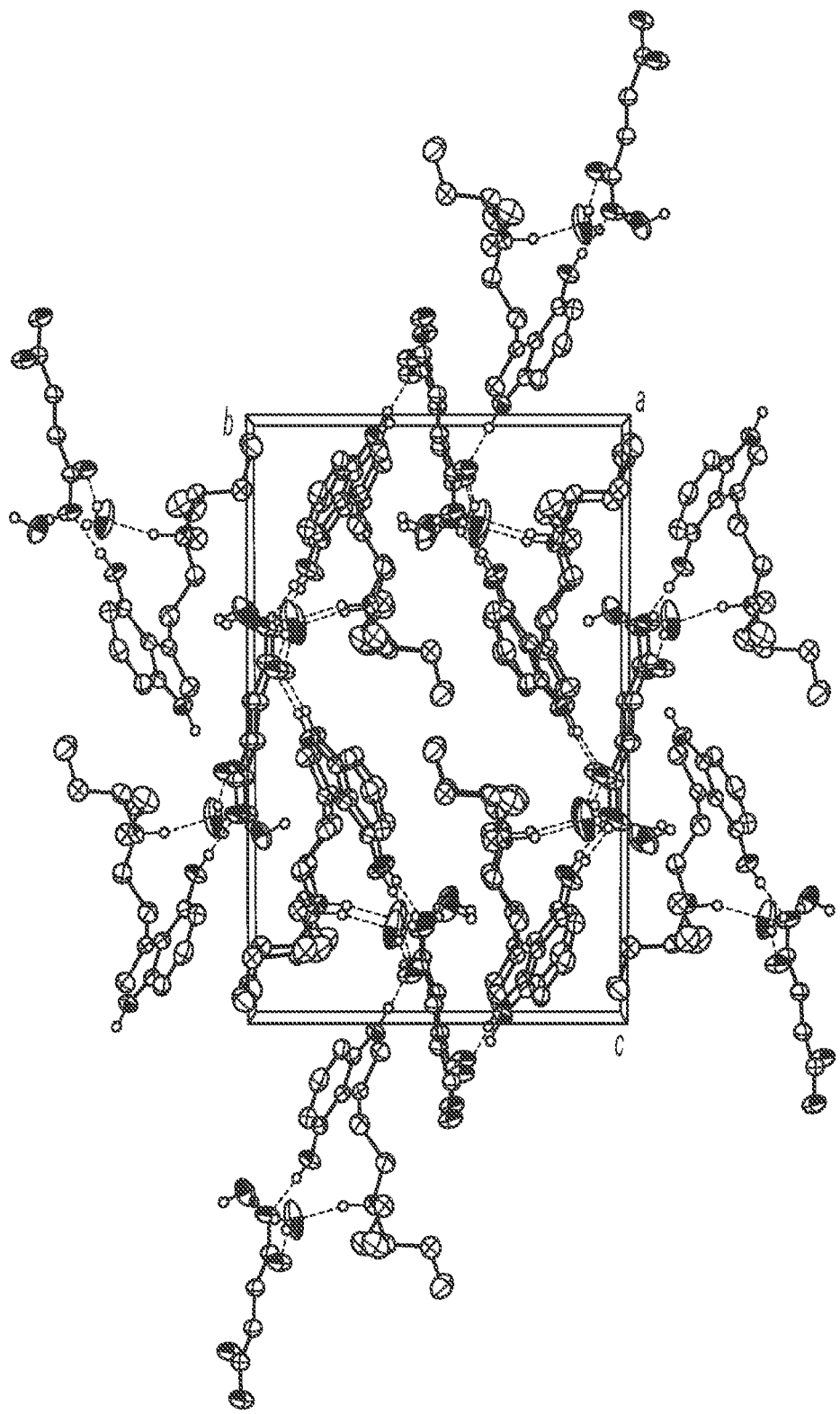
FIG. 3 shows the crystal packing of the 4-HO-DPT fumarate.4H$_2$O, viewed along the a axis.

FIG. 3 shows the crystal packing of crystalline 4-HO-DPT fumarate.4H$_2$O, viewed along the a axis. The N—H . . . O and O—H . . . O hydrogen bonds are shown as dashed lines. Displacement ellipsoids are drawn at the 50% probability level. Hydrogen atoms not involved in hydrogen bonding are omitted for clarity.

Figure 4:
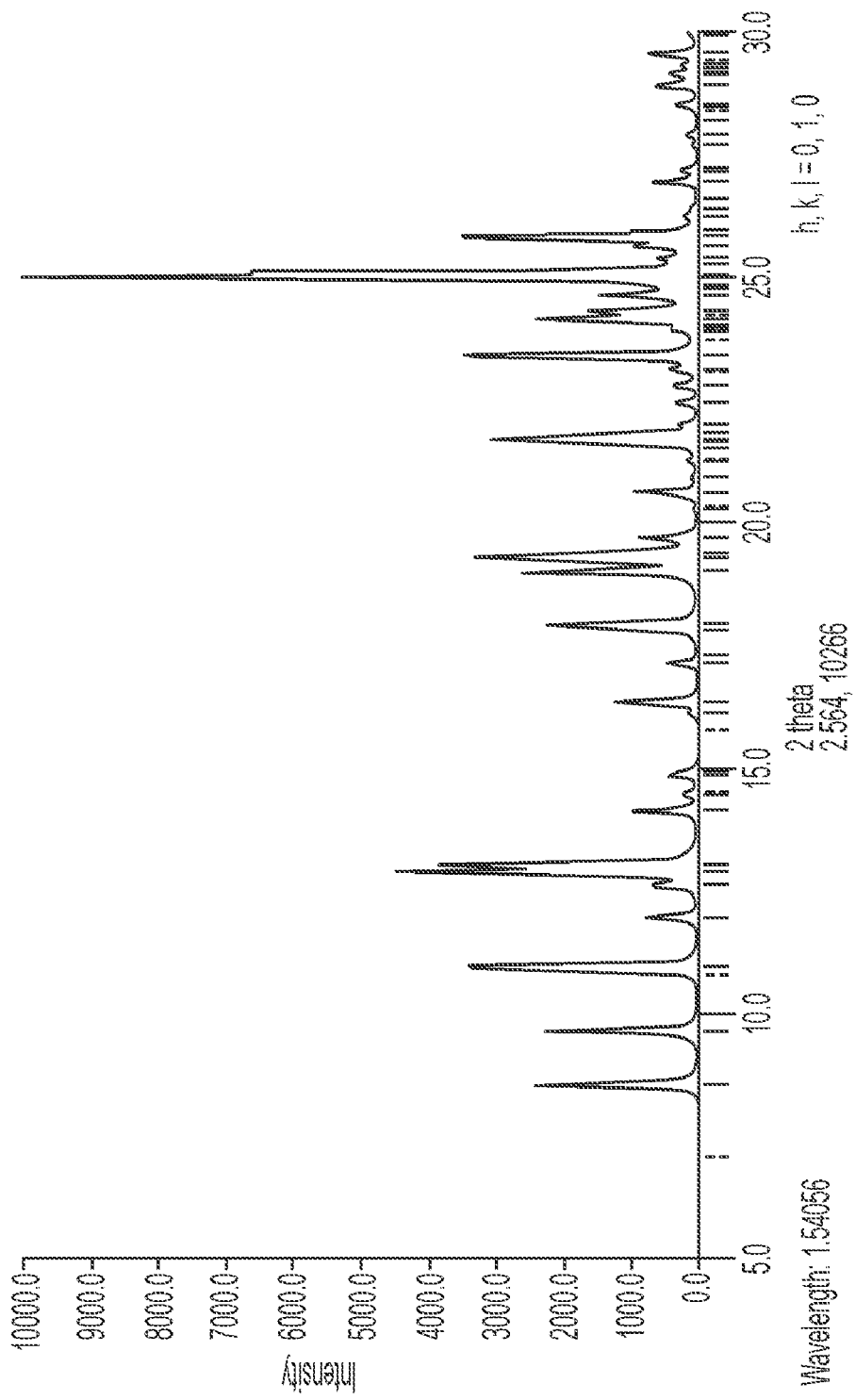
FIG. 4 shows a simulated X-ray powder diffraction pattern (XRPD) for 4-HO-DPT fumarate.4H$_2$O generated from its single crystal data.

Simulated Powder X-ray Diffraction (PXRD) Pattern. FIG. 4 shows a simulated X-ray powder diffraction pattern (XRPD) for crystalline 4-HO-DPT fumarate.4H$_2$O generated from its single crystal data. Table 4 lists the angles, °2θ±0.2°2θ, and d-spacing of the peaks identified in the experimental XRPD pattern of FIG. 4. The entire list of peaks, or a subset thereof, may be sufficient to characterize the cocrystal. For example, the cocrystal may be characterized by at least two peaks selected from the peaks at 8.5, 9.6, and 10.9°2θ±0.2°2θ or their corresponding d-spacing as well as by a XRPD pattern substantially similar to FIG. 4.

TABLE 4

| d-spacing (Å) | 2(Theta deg) | Intensity(%) |
|---|---|---|
| 10.33 | 8.5 | 2.8 |
| 9.16 | 9.6 | 3.2 |
| 8.07 | 10.9 | 6.3 |
| 7.39 | 12.0 | 1.6 |
| 7.01 | 12.6 | 1.2 |
| 6.86 | 12.9 | 10.6 |
| 6.78 | 13.0 | 9.1 |
| 6.26 | 14.1 | 3.0 |
| 5.96 | 14.8 | 1.3 |
| 5.41 | 16.4 | 5.1 |
| 5.17 | 17.1 | 2.2 |
| 4.97 | 17.8 | 1.1 |
| 4.97 | 17.8 | 4.2 |
| 4.95 | 17.9 | 10.0 |
| 4.67 | 19.0 | 14.3 |
| 4.60 | 19.3 | 14.3 |
| 4.58 | 19.4 | 12.7 |
| 4.51 | 19.7 | 4.7 |
| 4.30 | 20.6 | 6.4 |
| 4.18 | 21.3 | 1.0 |
| 4.09 | 21.7 | 23.4 |
| 4.07 | 21.8 | 2.7 |
| 4.04 | 22.0 | 1.6 |
| 3.96 | 22.4 | 2.5 |
| 3.90 | 22.8 | 3.0 |
| 3.84 | 23.1 | 3.0 |

TABLE 4-continued

| d-spacing (Å) | 2(Theta deg) | Intensity(%) |
|---|---|---|
| 3.80 | 23.4 | 30.5 |
| 3.72 | 23.9 | 2.3 |
| 3.68 | 24.2 | 20.9 |
| 3.66 | 24.3 | 13.0 |
| 3.61 | 24.6 | 12.5 |
| 3.58 | 24.8 | 3.5 |
| 3.55 | 25.0 | 100.0 |
| 3.50 | 25.4 | 4.0 |
| 3.47 | 25.6 | 5.5 |
| 3.47 | 25.7 | 2.3 |
| 3.44 | 25.8 | 36.8 |
| 3.39 | 26.3 | 1.6 |
| 3.37 | 26.4 | 1.0 |
| 3.30 | 27.0 | 7.8 |
| 3.28 | 27.2 | 2.3 |
| 3.27 | 27.2 | 1.0 |
| 3.22 | 27.7 | 1.3 |
| 3.19 | 27.9 | 2.6 |
| 3.13 | 28.5 | 4.3 |
| 3.08 | 28.9 | 1.5 |
| 3.08 | 28.9 | 7.4 |
| 3.06 | 29.1 | 5.7 |
| 3.05 | 29.2 | 1.0 |
| 3.04 | 29.4 | 3.1 |
| 3.02 | 29.6 | 11.0 |

Example 2: Preparation and Characterization of Bis(4-Hydroxy-N,N-Di-n-Propyltryptammonium) Chloride (4-HO-DPT Chloride)

Preparation. 4-hydroxy-N,N-di-n-propyl-tryptamine as its freebase (50 mg, 0.19 mmol) was dissolved in di-chloromethane, and 160 mL of hydrochloric acid (1.25 M in ethanol, 0.20 mmol) was added with stirring at room temperature. The mixture was stirred for 30 minutes, resulting in a white precipitate which was isolated via vacuum filtration and washed with di-ethyl ether to yield 28 mg of the salt. A second crop was collected by concentrating and cooling the filtrate to give another 13 mg of salt (73% yield). Crystals suitable for X-ray diffraction studies were grown from the slow evaporation of a methyl-ene chloride/methanol mixture. The sample was analyzed by nuclear magnetic resonance. $^1$H NMR (400 MHz, D$_2$O): d 7.07 (s, 1H, ArH), 7.04-6.96 (m, 2H, ArH), 6.47 (dd, J=6.1, 2.4 Hz, 1H, ArH), 3.42-3.30 (m, 2H, CH$_2$), 3.20-3.07 (m, 2H, CH$_2$), 3.00 (dd, J=10.1, 6.4 Hz, 4H, CH$_2$), 1.60 (h, J=6.8 Hz, 4H, CH$_2$), 0.84 (t, J=7.4 Hz, 6H, CH$_3$); 13C NMR (100 MHz, D$_2$O): d 149.9 (Ar), 138.8 (Ar), 123.3 (Ar), 123.2 (Ar), 115.9 (Ar), 108.5 (Ar), 104.5 (Ar), 103.7 (Ar), 54.7 (AkC), 53.7 (AkC), 21.2 (AkC), 16.8 (AkC), 10.0 (AkC).

Single Crystal Characterization. The single crystal data, data collection and structure refinement parameters for the crystalline structure of 4-HO-DPT chloride measured at 273 K are reported in Table 5, below.

TABLE 5

| Crystal data | |
|---|---|
| Cl·C$_{16}$H$_{25}$N$_2$O | Z = 2 |
| M$_r$ = 296.83 | F(000) = 320 |
| Triclinic, P$^-$1 | D$_x$ = 1.160 Mg m$^{-3}$ |
| a = 7.860(3) Å | Mo Ka radiation, I = 0.71073 Å |
| b = 10.439(4) Å | Cell parameters from 9206 reflections |
| c = 11.713(5) Å | q = 2.6-25.8° |
| a = 76.236(14)° | m = 0.22 mm$^{-1}$ |
| b = 73.653(13)° | T = 273 K |
| g = 68.852(12)° | Block, colourless |
| V = 850.0(6) Å$^3$ | 0.15 × 0.10 × 0.10 mm |
| Data collection | |
| Bruker D8 Venture CMOS diffractometer | 2756 reflections with I > 2s(I) |
| f and w scans | R$_{int}$ = 0.066 |
| Absorption correction: multi-scan SADABS2016/2 (Bruker, 2016/2) was used for absorption correction. wR2(int) was 0.0634 before and 0.0491 after correction. The Ratio of minimum to maximum transmission is 0.9659. The I/2 correction factor is Not present. | q$_{max}$ = 26.0°, q$_{min}$ = 2.6° |
| T$_{min}$ = 0.720, T$_{max}$ = 0.745 | h = −9 ⊛ 9 |
| 27008 measured reflections | k = −12 ⊛ 12 |
| 3243 independent reflections | l = −14 ⊛ 14 |
| Refinement | |
| Refinement on F$^2$ | 3 restraints |
| Least-squares matrix: full | Hydrogen site location: mixed |
| R[F$^2$ > 2s(F$^2$)] = 0.036 | H atoms treated by a mixture of independent and constrained refinement |
| wR(F$^2$) = 0.103 | w = 1/[s$^2$(F$_o^2$) + (0.0541P)$^2$ + 0.1743P] where P = (F$_o^2$ + 2F$_c^2$)/3 |
| S = 1.03 | (D/s)$_{max}$ = 0.001 |
| 3243 reflections | Dρ$_{max}$ = 0.43 e Å$^{-3}$ |
| 192 parameters | Dρ$_{min}$ = −0.40 e Å$^{-3}$ |

Figure 5:
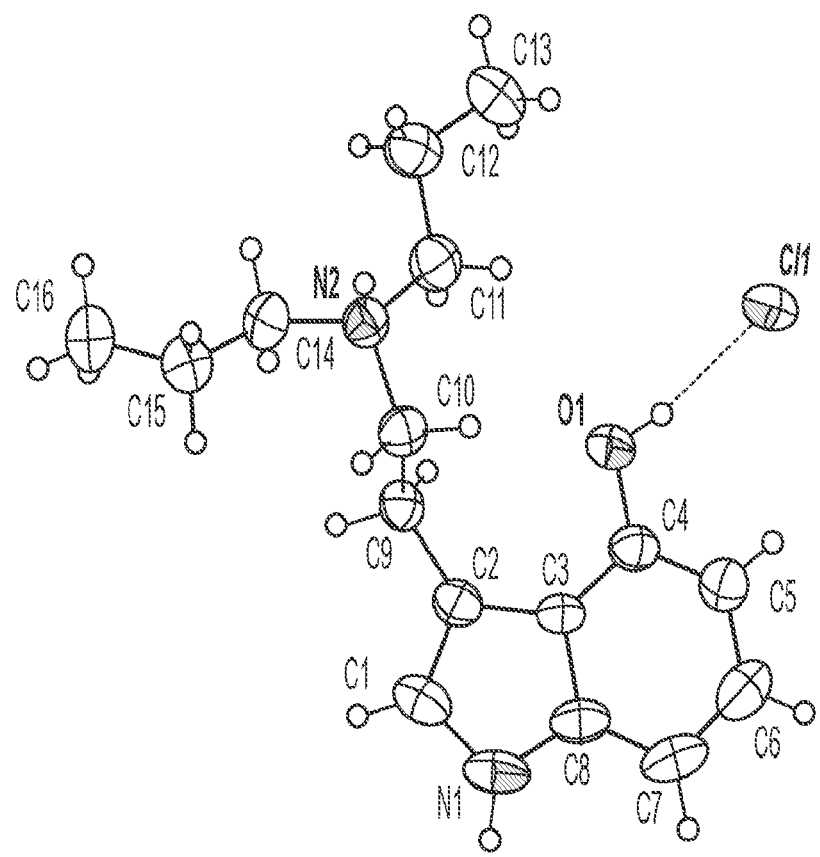
FIG. 5 shows the molecular structure of 4-HO-DPT chloride, showing atomic labelling.
Figure 6:
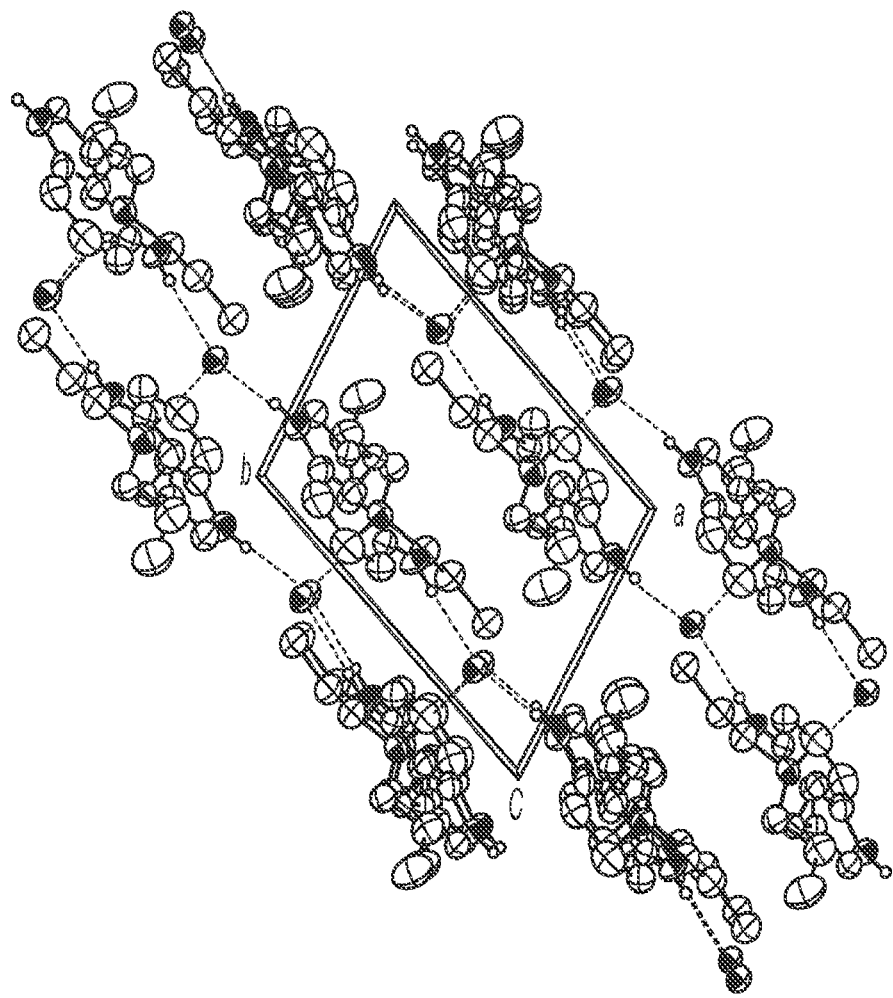
FIG. 6 shows the crystal packing of 4-HO-DPT chloride, viewed along the c axis.

FIG. 5 shows the molecular structure of crystalline 4-HO-DPT chloride, showing atomic labelling. Displacement ellipsoids are drawn at the 50% probability level. Hydrogen bonds are shown as dashed lines. FIG. 6 shows the crystal packing of crystalline 4-HO-DPT chloride, viewed along the c axis. The hydrogen bonds are shown as dashed lines. Displacement ellipsoids are drawn at the 50% probability level. Hydrogen atoms not involved in hydrogen bonds are omitted for clarity.

Figure 7:
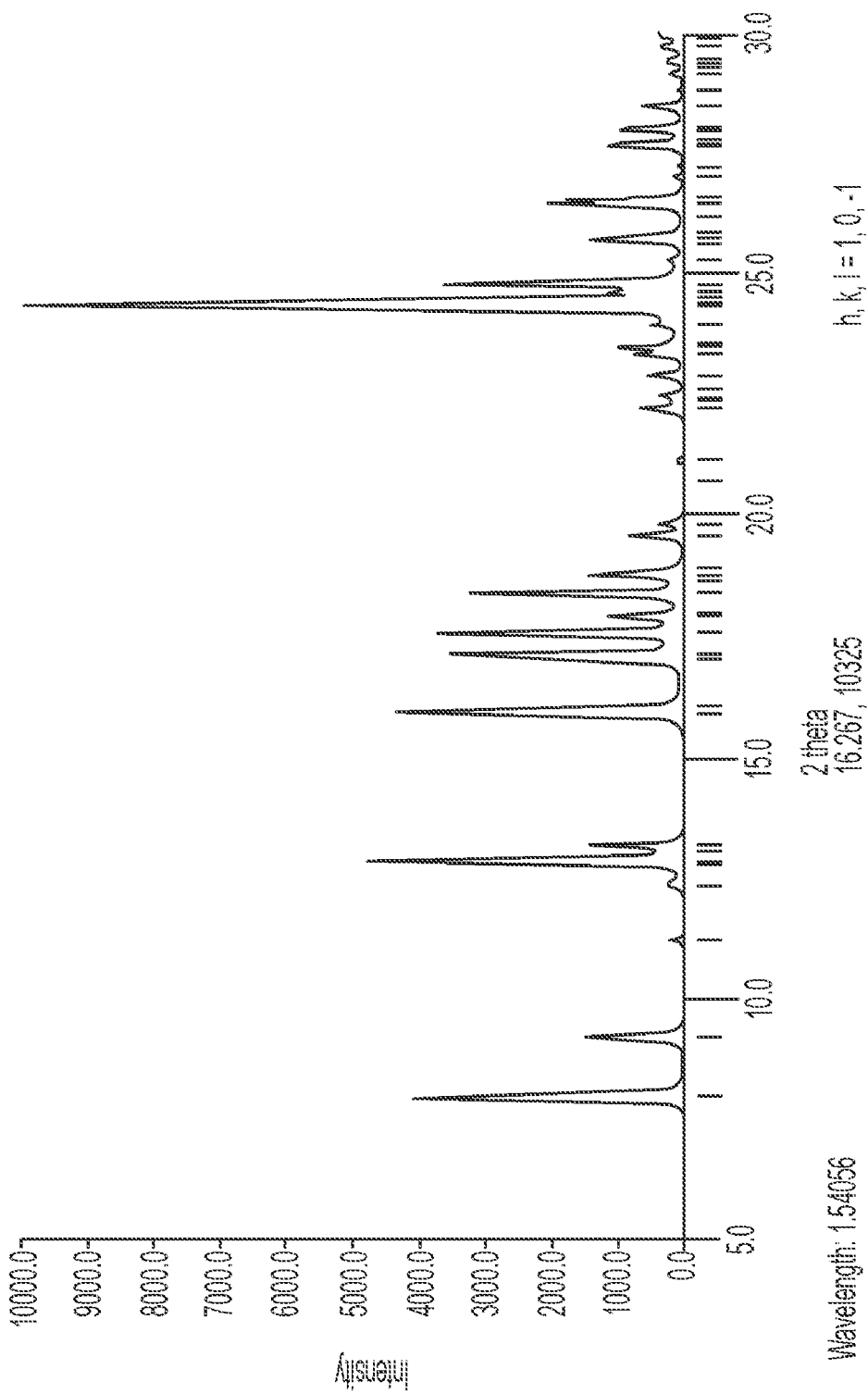
FIG. 7 shows a simulated X-ray powder diffraction pattern (XRPD) for 4-HO-DPT chloride generated from its single crystal data.

Simulated Powder X-ray Diffraction (PXRD) Pattern. FIG. 7 shows a simulated X-ray powder diffraction pattern (XRPD) for crystalline 4-HO-DPT chloride generated from its single crystal data. Table 4 lists the angles, °2θ±0.2° 2θ, and d-spacing of the peaks identified in the experimental XRPD pattern of FIG. 7. The entire list of peaks, or a subset thereof, may be sufficient to characterize the cocrystal. For example, the cocrystal may be characterized by at least two peaks selected from the peaks at 8.0, 9.2, and 15.9°2θ±0.2°2θ or their corresponding d-spacing as well as by a XRPD pattern substantially similar to FIG. 7.

TABLE 6

| d-spacing (Å) | 2Theta (deg) | Intensity |
|---|---|---|
| 11.11 | 8.0 | 1951.6 |
| 9.62 | 9.2 | 932.538 |
| 7.89 | 11.2 | 215.308 |
| 7.16 | 12.4 | 269.01 |
| 6.90 | 12.8 | 178.991 |
| 6.87 | 12.9 | 6069.2 |
| 6.71 | 13.2 | 1724.83 |
| 5.55 | 15.9 | 8329.62 |
| 5.50 | 16.1 | 603.362 |
| 5.20 | 17.0 | 3072.42 |
| 5.16 | 17.2 | 4782.32 |
| 5.16 | 17.2 | 2854.28 |
| 5.03 | 17.6 | 8843.02 |
| 4.93 | 18.0 | 2629.92 |
| 4.91 | 18.0 | 2.56284 |
| 4.81 | 18.4 | 8311.82 |
| 4.71 | 18.8 | 3680.26 |
| 4.68 | 18.9 | 604.62 |
| 4.52 | 19.6 | 2355.68 |
| 4.47 | 19.9 | 1069.238 |
| 4.19 | 21.2 | 324.944 |
| 3.99 | 22.3 | 2353.14 |
| 3.96 | 22.4 | 286.524 |
| 3.95 | 22.5 | 1327.304 |
| 3.87 | 23.0 | 2090.94 |
| 3.80 | 23.4 | 2770.06 |
| 3.78 | 23.5 | 4178.04 |
| 3.76 | 23.6 | 103.6398 |
| 3.70 | 24.0 | 1528.18 |
| 3.65 | 24.4 | 2033.62 |
| 3.64 | 24.4 | 42964 |
| 3.64 | 24.4 | 3392.82 |
| 3.62 | 24.5 | 501.526 |
| 3.62 | 24.6 | 2689.16 |
| 3.60 | 24.7 | 2292.5 |
| 3.58 | 24.9 | 16641.26 |
| 3.51 | 25.3 | 846.002 |
| 3.46 | 25.7 | 389.192 |
| 3.45 | 25.8 | 5132.62 |
| 3.45 | 25.8 | 2405.72 |
| 3.44 | 25.9 | 666.476 |
| 3.36 | 26.5 | 10631.96 |
| 3.35 | 26.6 | 2406.26 |
| 3.30 | 27.1 | 467.052 |
| 3.27 | 27.3 | 244.45 |
| 3.21 | 27.7 | 6095.62 |
| 3.21 | 27.8 | 744.012 |
| 3.21 | 27.8 | 162.6998 |
| 3.18 | 28.1 | 515.842 |
| 3.18 | 28.1 | 5309.02 |
| 3.13 | 28.5 | 3906.82 |
| 3.09 | 28.9 | 282.574 |

TABLE 6-continued

| d-spacing (Å) | 2Theta (deg) | Intensity |
|---|---|---|
| 3.05 | 29.2 | 592.194 |
| 3.05 | 29.2 | 542.544 |
| 3.03 | 29.4 | 82.4986 |
| 3.03 | 29.5 | 394.276 |
| 3.02 | 29.5 | 1349.174 |
| 3.00 | 29.8 | 2329.26 |
| 2.98 | 30.0 | 286.794 |

REFERENCES

Bruker (2016). APEX3, SAINT, and SADABS. Bruker AXS Inc., Madison, Wisconsin, USA.
Carhart-Harris, R. L & Goodwin, G. M. (2017). Neuropsychopharmacology, 42, 2105-2113.
Chadeayne, A. R., Golen, J. A. & Manke, D. R. (2019a). Acta Cryst. E75, 900-902.
Chadeayne, A. R., Golen, J. A. & Manke, D. R. (2019b). IUCrData, 4, x190962.
Chadeayne, A. R., Golen, J. A. & Manke, D. R. (2019c). Psychedel. Sci. Rev. https://psychedelicreview.com/the-crystal-structure-of-4-aco-dmt-fumarate/.
Chadeayne, A. R., Pham, D. N. K., Golen, J. A. & Manke, D. R. (2019). Acta Cryst. E75, 1316-1320.
Dolomanov, O. V., Bourhis, L J., Gildea, R. J., Howard, J. A. K. & Puschmann, H. (2009). J. Appl. Cryst. 42, 339-341.
Falkenberg, G. (1972). Acta Cryst. B28, 3075-3083.
Petcher, T. J. & Weber, H. P. (1974). J. Chem. Soc. Perkin Trans. 2, pp. 946-948.
Repke, D. B., Ferguson, W. J. & Bates, D. K. (1977). J. Heterocycl. Chem. 14, 71-74.
Sheldrick, G. M. (2015a). Acta Cryst. A71, 3-8.
Sheldrick, G. M. (2015b). Acta Cryst. C71, 3-8.
Shulgin, A. T., & Shulgin, A. (1997). Tihkal. La Fayette: Transform Press.
Weber, H. P. & Petcher, T. J. (1974). J. Chem. Soc. Perkin Trans. 2, pp. 942-946.
Westrip, S. P. (2010). J. Appl. Cryst. 43, 920-925.

The claimed invention is:

1. Crystalline 4-hydroxy-N,N-di-n-propyl-tryptammonium chloride characterized by at least one of:
   a triclinic, P⁻1 at a temperature of about 273 K;
   unit cell dimensions a=7.860 (3) Å, b=10.439 (4) Å, c=11.713 (5) Å, α=76.236 (14)°, β=73.653 (13)°, and γ=68.852 (12)°;
   an X-ray powder diffraction pattern substantially similar to FIG. 7; or
   an X-ray powder diffraction pattern characterized by at least two peaks selected from 8.0, 9.2, and 15.9°2θ±0.2°2θ.

2. A composition comprising crystalline 4-hydroxy-N,N-di-n-propyl-tryptammonium chloride according to claim 1 and an excipient.

3. A composition comprising crystalline 4-hydroxy-N,N-di-n-propyl-tryptammonium chloride according to claim 1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, or (i) a purified hericenone.

4. A method of treating a psychological disorder comprising the step of:
   administering to a subject in need thereof a therapeutically effective amount of crystalline 4-hydroxy-N,N-di-n-propyl-tryptammonium chloride according to claim 1,
wherein the psychological disorder is selected from the group consisting of depression and post-traumatic stress disorder (PTSD).

5. A method of treating pain comprising the step of:
   administering to a subject in need thereof a therapeutically effective amount of crystalline 4-hydroxy-N,N-di-n-propyl-tryptammonium chloride according to claim 1.

* * * * *